United States Patent [19]

Jones et al.

[11] 4,323,487

[45] Apr. 6, 1982

[54] ABSORBENT STARCH GRAFT POLYMER AND METHOD OF ITS PREPARATION

[75] Inventors: Duane A. Jones, Minneapolis; Lyle F. Elmquist, St. Paul, both of Minn.

[73] Assignee: Henkel Corporation, Minneapolis, Minn.

[21] Appl. No.: 87,682

[22] Filed: Oct. 22, 1979

[51] Int. Cl.$^3$ ............................................... C08L 3/04
[52] U.S. Cl. .................................................. 525/54.32
[58] Field of Search ................................. 260/17.46 C

[56] References Cited

U.S. PATENT DOCUMENTS

| | | | |
|---|---|---|---|
| 3,669,915 | 6/1972 | Jones | 260/17.46 C |
| 3,785,921 | 1/1974 | Ide et al. | 162/168 |
| 3,862,028 | 1/1975 | Jones et al. | 260/17.46 C |
| 3,935,099 | 1/1976 | Weaver et al. | 260/17.46 C |
| 3,981,100 | 9/1976 | Weaver et al. | 260/17.46 C |
| 3,985,616 | 10/1976 | Weaver et al. | 260/17.46 C |
| 3,997,484 | 12/1976 | Weaver et al. | 260/17.46 C |
| 4,051,086 | 9/1977 | Reid | 260/17.46 C |
| 4,069,177 | 1/1978 | Smith | 260/17.46 C |
| 4,076,663 | 2/1978 | Masuda et al. | 260/17.46 C |
| 4,079,025 | 3/1978 | Young et al. | 260/17.46 C |
| 4,123,397 | 10/1978 | Jones | 260/17.46 C |
| 4,134,863 | 1/1979 | Fanta | 260/17.46 C |
| 4,159,260 | 6/1979 | Jones et al. | 260/17.46 C |

FOREIGN PATENT DOCUMENTS 44-12879  6/1969  Japan .

*Primary Examiner*—V. P. Hoke
*Attorney, Agent, or Firm*—Dorsey, Windhorst, Hannaford, Whitney & Halladay

[57] ABSTRACT

A water absorbent composition and method of preparing the same having improved wicking characteristics and comprising a combination of hydrolyzed starch polyacrylonitrile graft copolymer and a source of formaldehyde.

15 Claims, No Drawings

ABSORBENT STARCH GRAFT POLYMER AND METHOD OF ITS PREPARATION

The present invention relates generally to a highly absorbent composition having improved wicking characteristics. More particularly, the present invention relates to a composition comprising hydrolyzed starch polyacrylonitrile graft copolymer which has been reacted with a guantity of formaldehyde. This composition exhibits significantly improved wicking properties while retaining acceptable levels of absorbency.

BACKGROUND OF THE INVENITON

Hydrolyzed starch polyacrylonitrile graft copolymers which exhibit the capacity to absorb from about 300 to 1000 times their weight of deionized water are known at this time. The development of these compositions was carried out by the Northern Regional Research Laboratory, Peoria, Ill. The hydrolyzed starch polyacrylonitrile graft copolymer is produced by the free radical method of polymerization. In this method, starch, either gelatinized or ungelatinized, is exposed to a catalyst such as ceric ammonium nitrate which acts as a catalyst to generate free radicals in the starch chain. These free radicals can also be produced by radiation. Polyacrylonitrile chains become attached to these free radicals by copolymerization. A wide range of substitution in these copolymers is known in the art. For example, U.S. Pat. No. 3,035,099 shows the preparation of copolymers in which the starch to polyacrylonitriles molar ratios range from 1:1.5 to 1:9. The variations in molar ratio of the components of the copolymer is not critical to the practice of this invention. The resulting material is then saponified in sodium hydroxide to hydrolyze the polyacrylonitrile chains to carboxamide and alkali metal carboxylate groups mixed with metal salts. Drying the hydrolyzed material can be accomplished by tumble air drying or vacuum drying. After drying, the material can absorb about 300 to 400 times its weight of deionized water. Washing the absorbent polymer before drying with alcohol increases its absorbency to 800 to 1000 times its weight of deionized water.

The absorbent polymer can be made as film, flakes, powder or mat. These forms take up water, swelling but not dissolving and hold it in expanded duplications of their own dry shapes. Films extend and thicken in all dimensions. Powders become piles of water textured like crushed ice. A flake expands to a clear, angular piece of water. The swollen forms shrink in dilute acid, expand again in dilute alkali solution. They also shrink as they dry and expand again when absorbing water.

The absorbent polymer, with these properties, can be mixed with or coated on a wide variety of materials including, for example, sand, straw, sawdust, seeds and roots, natural or synthetic fibers, flour, gelatin and starch. It can hold water in soils, animal bedding and kitty litter, toweling and diapers, bandages, surgical pads and dental absorbents.

On addition to aqueous fluids, the absorbent polymer swells rapidly, absorbing the aqueous fluid in the process. The rate of swelling (hydration rate) and the amount of fluid capable of being absorbed varies with the dissolved ion content of the fluid; however, the hydration rate and volume absorbed are significant even with relatively high ion content fluids.

While rapid hydration rates and a high degree of absorbency of the absorbent polymer are desirable in many applications, the rapid rate of hydration can be a disadvantage when aqueous fluid is added to the dry, hydrolyzed starch polyacrylonitrile graft copolymer powder. In this case, the surface of the quantity of absorbent polymer powder in contact with aqueous fluid swells and absorbs the fluid so quickly that the resulting swollen gel reduces or blocks further penetration of the aqueous fluid. This, in turn, reduces or retards full swelling or absorbency of the product. In some cases wet-out of the dry product can be improved by increasing granulation of the product, but large granular material is not always feasible and even when it is, the improvement is only partial. Thus, a need exists for a highly absorbent product which wets-out quickly and completely when exposed to an aqueous fluid, but which still retains acceptable absorbency characteristics.

Applicants are aware of the teachings of the Reid Pat. No. 4,051,086 regarding the use of a difunctional dialdehyde, glyoxal, as a crosslinking agent in the modification of a crosslinked grafted polysaccharide to improve the wicking characteristics of an absorbent polymer. As further taught in the Reid patent, however, while glyoxal appears to be effective for the materials contemplated therein, it does not appear to be effective in improving the wicking of other crosslinked absorbent derivatives. In fact, it does not appear to be effective with hydrolyzed starch polyacrylonitrile graft copolymer, the absorbent polymer contemplated by the present invention.

SUMMARY OF THE INVENTION

According to the present invention, it has been found that by reducing the hydration rate or the rate of product swelling of hydrolyzed starch polyacrylonitrile graft copolymer, significantly improved wicking or wet-out characteristics can be achieved. This can be accomplished by reacting the hydrolyzed starch polyacrylonitrile graft copolymer with a quantity of formaldehyde. The resulting composition is hydrolyzed starch polyacrylonitrile graft copolymer which is crosslinked with formaldehyde.

DETAILED DESCRIPTION OF THE INVENTION

As described above, the hydrolyzed starch polyacrylonitrile graft copolymer is prepared from starch by: (1) polymerization of acrylonitrile onto starch, and (2) alkaline hydrolysis to convert the nitrile groups to carboxamide and carboxylate groups. Thus, hydrolyzed starch polyacrylonitrile graft copolymer is technically a graft terpolymer of starch, acrylamide and alkali metal acrylate. For the purpose of describing the present invention, it will be referred to as hydrolyzed starch polyacrylonitrile graft copolymer or simply the absorbent polymer. Conventionally, the polyacrylonitrile portion of the starch graft polyacrylonitrile copolymer may be hydrolyzed with alkali in water after which the graft terpolymer is precipitated by the addition of methanol or other suitable precipitating agent allowing the graft terpolymer to be mechanically separated. The graft terpolymer is then neutralized and dried. The remaining details of preparing hydrolyzed starch polyacrylonitrile graft polymer are well known in the art.

The hydrolyzed starch polyacrylonitrile graft polymer is highly absorbent of aqueous fluids, being capable of absorbing up to 1000 times its own weight of deionized water. In addition to its high absorbency characteristics, it also exhibits extremely fast absorbency or hydration rates. In fact, the product swells so quickly that in an aqueous fluid with minimal agitation, the swollen gel-like substance which forms on the surface of the dry absorbent polymer powder reduces or blocks further penetration of the aqueous fluid. Thus, although it has excellent absorbent characteristics, hydrolyzed starch polyacrylonitrile graft copolymer has inadequate wicking or wet-out properties. Absorptivity of a particular composition can be determined by hydrating a weighed amount of material in the fluid being tested (usually either deionized water or 1% NaCl), pouring the water and hydrated material onto a sieve and weighing the amount of fluid which passes through the sieve. The amount of fluid held by the absorbent composition is then calculated as grams of fluid per gram of absorbent composition. The absorptivity of the hydrolyzed starch polyacrylonitrile graft copolymer can be as high as 1000 grams of deionized water or 80 grams of 1% NaCl solution per gram of absorbent polymer.

The wicking ability of a composition can be determined by placing a given quantity (in this case 0.1 gram) of the composition onto wet filter paper in contact with a perforated disc floating in deionized water. The time required for the quantity of product to completely wet out is the wicking time. The wicking time of hydrolyzed starch polyacrylonitrile graft copolymer using the above procedure can be as long as several hours. Thus, the wicking ability of this absorbent polymer is relatively poor. By reacting the hydrolyzed starch polyacrylonitrile graft copolymer with formaldehyde in accordance with the present invention, however, the wicking time can be significantly reduced.

It is believed that the reaction of formaldehyde with hydrolyzed starch polyacrylonitrile graft copolymer results in controlled crosslinking of the absorbent polymer complex. It is believed that this crosslinking ties up parts of the very large absorbent polymer molecule to reduce the absorbency and absorbency rate and thus improve the wicking properties. If enough formaldehyde is reacted, the wicking time using the above procedure can be reduced to a matter of seconds so that wicking is almost instantaneous. With this reduction in wicking time, however, comes a reduction in absorptivity. Thus, as the wicking properties are improved by the reaction with formaldehyde, the total absorptivity is reduced. While there are uses for absorbent compositions having wicking times and absorption properties which vary throughout the entire spectrum of possibilities, from the very high absorption properties and slow wicking times of hydrolyzed starch polyacrylonitrile graft copolymer to the very fast wicking times and low absorption properties of absorbent polymer--formaldehyde compositions, a preferred composition is one in which the wicking time according to the above procedure is less than about five minutes and the absorptivity is greater than about 30 grams of 1% NaCl solution per gram of composition.

The formaldehyde can be introduced at various stages during preparation of the absorbent polymer. For example, it can be reacted with the dry absorbent polymer, introduced into an alcohol suspension of graft terpolymer or with the isolated alcohol-water wet hydrolyzate or added concurrently with the alkaline hydrolyzing agent. It can also be reacted under various conditions. The specific amount of formaldehyde reacted with the absorbent polymer will depend upon a number of factors: (1) the stage at which the formaldehyde is reacted with the absorbent polymer, (2) the conditions under which it is reacted, and (3) the desired characteristics of the final product. The amount of crosslinking achieved by reaction of the absorbent polymer with the formaldehyde cannot be measured directly by conventional analytical methods. Consequently, the crosslinking reaction is controlled by measuring the proportions of reactants used and monitoring by process control methods such as absorbency rate (wicking) and absorbent capacity tests.

Preferably, the formaldehyde is reacted with the dry granular form of hydrolyzed starch polyacrylonitrile graft copolymer. With this procedure, the source of formaldehyde is conveniently added in a dry granular or powder form as paraformaldehyde. As is known in the art, paraformaldehyde is simply the solid polymer of formaldehyde which depolymerizes into gaseous formaldehyde upon heating. For all practical purposes and for the purposes of the present invention, depolymerization of a given quantity of paraformaldehyde will yield a substantially equivalent weight of formaldehyde. The combination of dry absorbent polymer and paraformaldehyde is then heated to a temperature sufficient to break down and depolymerize the paraformaldehyde, thus creating conditions for the crosslinking reaction. The characteristics of the resulting product will vary with the amount of crosslinking caused by the formaldehyde. In general, however, as the degree of crosslinking increases, the absorbency decreases and the wicking properties improve.

Dry hydrolyzed starch polyacrylonitrile graft copolymer has been reacted with quantities of paraformaldehyde in the above procedure as low as 0.1% by weight and as high as 6.0% by weight of the absorbent polymer. In general, quantities of paraformaldehyde below approximately 0.25% by weight do not stimulate enough crosslinking to improve the wicking properties to a point where the wicking time is less than five minutes. On the other hand, quantities of paraformaldehyde above approximately 2.0% by weight of the copolymer result in excellent wicking properties, but a reduction in total absorbency characteristics below approximately 20 grams of NaCl solution per gram of composition. While absorbent compositions of the type covered by the present invention can have varying absorbency and wicking characteristics, the specific characteristics desired depend upon the use for which the composition is intended. A composition with particularly desirable characteristics, however, is a composition having a wicking time of less than about five minutes and absorbency greater than about 30 grams of NaCl solution per gram of composition. This results from reaction of the hydrolyzed starch polyacrylonitrile graft copolymer with between about 0.25% and 1.25% by weight formaldehyde.

The temperature at which the combination is heated in the above procedure can vary. It must, however, be sufficiently high to break down and depolymerize the paraformaldehyde, but not so high as to adversely affect either the paraformaldehyde or the absorbent polymer. It has been found that mixing starch-hydrolyzed polyacrylonitrile graft copolymer and paraformaldehyde and then heating in a closed system to a temperature of about 100° C. for four and one-half hours results in an acceptable composition. Generally, the higher the temperature, the shorter the necessary exposure time, while the lower the temperature, the longer the exposure time. Temperatures between about 80° C. and 150° C. have been found acceptable.

Hydrolyzed starch polyacrylonitrile graft copolymer and paraformaldehyde have also been combined by adding paraformaldehyde to the dry absorbent polymer mixed with isopropyl alcohol to form a wet cake which was then dried. This method also requires some heating to depolymerize the paraformaldehyde. However, because much of the paraformaldehyde upon depolymerization is believed to be consumed in side reactions, a greater quantity of paraformaldehyde must be used. A quantity of paraformaldehyde of approximately 6% by weight reacted in this manner resulted in a product with wicking time of less than five minutes and absorbency of greater than 30 grams of 1% NaCl solution per gram of composition.

Formaldehyde can also be reacted with the starch polyacrylonitrile graft copolymer prior to completion of the hydrolyzing, isolation and drying steps. Specifically, formaldehyde can be added after hydrolysis and isolation of the hydrolyzed copolymer or formaldehyde can be added directly to the hydrolyzate, but before isolation and drying. While both procedures result in compositions having acceptable properties, both of these procedures also require more formaldehyde than reacting dry paraformaldehyde directly with dry absorbent polymer. This is particularly true when adding formaldehyde directly to the hydrolyzate where approximately 15% by weight formaldehyde is needed to produce a composition with an acceptable wicking time. The additional quantity of formaldehyde is needed when adding it to the absorbent polymer at these points because of the increasing difficulty in obtaining crosslinking and the fact that much of the formaldehyde reacts with itself to form methyl alcohol and formic acid (sodium formate) in the alkaline system. When dry paraformaldehyde is added to dry copolymer in the presence of heat, however, it is believed that nearly all of the formaldehyde reacts with the absorbent polymer to perform a crosslinking function.

Thus, in procedures requiring quantities of formaldehyde or paraformaldehyde greater than the qunatities of paraformaldehyde required in the procedure involving the reaction of dry paraformaldehyde with dry absorbent polymer, it is believed the excess is consumed in side reactions. Accordingly, regardless of the route taken to obtain the resulting composition, it is believed that compositions having similar wicking and absorbency characteristics have substantially equivalent formaldehyde components or substantially equivalent crosslinking caused by formaldehyde.

The following specific examples illustrate the preparation and testing of the composition of the present invention involving a combination of hydrolyzed starch polyacrylonitrile graft copolymer and formaldehyde.

EXAMPLE 1

Four lots of a hydrolyzed starch polyacrylonitrile graft copolymer sold under the trade name SGP® 502S by Henkel Corporation were each mixed with 0.75% paraformaldehyde (based on weight of SGP 502S), placed in a drying dish, covered and placed in 100° C. forced air oven for 4½ hours. The treated material was then passed through 30 mesh for testing.

Wicking properties were determined by dropping 0.01 gram of treated product onto wet filter paper in contact with a perforated disk floating in deionized water. The time required for the product to completely wet out is the wicking time. Absorbency of the treated products was determined by hydrating a weighed amount of material in the fluid being tested (deionized water or 1% NaCl), pouring onto a sieve and weighing the amount of fluid passing through. The amount of fluid held by the absorbent was then determined and from this the grams of fluid absorbed per gram of absorbent was calculated.

The wicking properties and fluid absorbencies of several lots of SGP 502S treated above are summarized in the following table.

| Lot | Wicking Time | Absorbency, 1% NaCl, g/g |
|---|---|---|
| 1 | 2 minutes, 12 seconds | 32 |
| 2 | 5 minutes | 31 |
| 3 | 58 seconds | 27 |
| 4 | 1 minute, 18 seconds | 26 |

Untreated SGP 502S had a wicking time of over 30 minutes.

EXAMPLE 2

SGP 502S (Lot 1) was treated as in Example 1 except the paraformaldehyde level was varied from 0.1% to 6.0% (based on weight of SGP 502S). Products were tested as in Example 1 with the following results.

| Paraformaldehyde Level | Wicking Time | Absorbency, 1% NaCl, g/g |
|---|---|---|
| 0 (blank) | 30 min. + | 68 |
| 0.10% | 10 min. + | 53 |
| 0.25% | about 5.5 min. | 41 |
| 0.50% | about 4 min. | 38 |
| 0.75% | 2 min. 45 sec. | 35 |
| 1.00% | 53 sec. | 27 |

| Paraformaldehyde Level | Wicking Time | Absorbency, 1% NaCl, g/g |
|---|---|---|
| 1.25% | 28 sec. | 26 |
| 1.50% | 15 sec. | 23 |
| 2.00% | 11 sec. | 20 |
| 3.00% | 6 sec. | 16 |
| 6.00% | almost instant | 11 |

EXAMPLE 3

SGP 502S was mixed with 6.0% paraformaldehyde (based on weight of SCP 502S) and 40% isopropyl alcohol (based on weight of SGP 502S) to form a wet cake. The absorbed wet material was added to a drying dish, covered and placed in an 80° C. forced air oven for 1½ hours. At this time, the dish was uncovered and drying carried out overnight. Treated material was then passed through 30 mesh and tested as in Example 1 with the following results.

| Lot | Wicking Time | Absorbency, 1% NaCl, g/g |
|---|---|---|
| 1 | 2 minutes, 34 seconds | 34 |
| 2 | 5 minutes + | 40 |
| 3 | about 5 minutes | 35 |
| 4 | 1 minute, 24 seconds | 27 |

EXAMPLE 4

SGP 502S wet cake (58% solids in methyl alcohol/water) and 4.63% paraformaldehyde (based on starting solids) were added to a flash evaporator and mixed for 5 minutes at room temperature with no vacuum. The evaporator flask was then placed in an 80° C. bath and heated for one hour without vacuum followed by cooling in a cold water bath. The evaporator flask was then placed in a 50° C. bath with vaccum for 15 minutes, the temperature raised to 80° C. and this temperature maintained for 15 minutes more. The evaporator flask was allowed to cool and the dried solids passed through 30 mesh. This product was tested as in Example 1 with the following results.

| Wicking Time | Absorbency, 1% NaCl, g/g |
| --- | --- |
| 13 seconds | 33 |

EXAMPLE 5

A starch/polyacrylonitrile graft copolymer was base hydrolyzed in a steam heated mixer and the resulting hydrolyzate cooled to 85° C. At this point, 14.8% formaldehyde was added (based on starting starch polyacrylonitrile graft copolymer solids) and mixing continued for 30 minutes. The solids were isolated by precipitation of the hydrolyzate with methyl alcohol. After washing and neutralization the solids were filtered and dried at 80° C. The solids were passed through 30 mesh and tested as described in Example 1 with the following results.

| Wicking | Absorbency, 1% NaCl, g/g | Absorbency, Deionized Water, g/g |
| --- | --- | --- |
| 1 min., 10 sec. | 37 | 151 |

We claim:

1. Hydrolyzed starch polyacrylonitrile graft copolymer which has been crosslinked with a quantity of formaldehyde comprising about 0.1% to 6.0% by weight of the hydrolyzed starch polyacrylonitrile graft copolymer.

2. The hydrolyzed starch polyacrylonitrile graft copolymer of claim 1 which has been crosslinked with a quantity of formaldehyde comprising about 0.25% to 1.25% by weight.

3. A water absorbent composition comprising hydrolyzed starch polyacrylonitrile graft copolymer which has been crosslinked with a quantity of formaldehyde comprising about 0.1% to 6.0% by weight.

4. The water absorbent composition of claim 3 in which the quantity of formaldehyde comprises about 0.25% to 1.25% by weight.

5. A water absorbent composition prepared by combining hydrolyzed starch polyacrylonitrile graft copolymer with formaldehyde in sufficient concentration to result in reaction between said hydrolyzed starch polyacrylonitrile graft copolymer and about 0.1% to 6.0% by weight of formaldehyde.

6. The water absorbent composition of claim 5 prepared by reaction between hydrolyzed starch polyacrylonitrile graft copolymer and about 0.25% to 1.25% by weight of formaldehyde.

7. The water absorbent composition of claim 6 wherein said formaldehyde is provided in the form of paraformaldehyde.

8. A method of preparing a water absorbent composition comprising reacting hydrolyzed starch polyacrylonitrile graft copolymer with a quantity of formaldehyde in the amount of about 0.1% to 6.0% by weight and at a temperature of between about 80° C. and 150° C.

9. The method of claim 8 wherein said formaldehyde is in sufficient concentration to result in reaction between said hydrolyzed starch polyacrylonitrile graft copolymer and between about 0.25% and 1.25% by weight of formaldehyde.

10. The method of claim 8 wherein said formaldehyde is combined with the hydrolyzed starch polyacrylonitrile graft copolymer hydrolyzate.

11. The method of claim 8 wherein said formaldehyde is combined with the hydrolyzed starch polyacrylonitrile graft copolymer in the wet cake form.

12. A method of preparing a water absorbent composition comprising reacting hydrolyzed starch polyacrylonitrile graft copolymer with formaldehyde wherein said formaldehyde is provided in the form of paraformaldehyde and is in sufficient concentration to result in reaction between said hydrolyzed starch polyacrylonitrile graft copolymer and about 0.25% to 1.25% by weight of formaldehyde and wherein said reaction is carried out at a temperature sufficient to depolymerize the paraformaldehyde.

13. The method of claim 12 including reacting dry hydrolyzed starch polyacrylonitrile graft copolymer with dry paraformaldehyde.

14. The method of claim 13 wherein said temperature is about 80° C. to 150° C.

15. The method of claim 14 wherein said temperature is about 100° C.

* * * * *